United States Patent

Tadanier et al.

[11] 4,331,804
[45] May 25, 1982

[54] 2-EPI-FORTIMICIN A AND DERIVATIVES

[75] Inventors: John S. Tadanier, Waukegan, Ill.; Robert Hallas, Kenosha, Wis.; Jerry R. Martin, Waukegan, Ill.

[73] Assignee: Abbott Laboratories, North Chicago, Ill.

[21] Appl. No.: 79,130

[22] Filed: Sep. 26, 1979

Related U.S. Application Data

[63] Continuation-in-part of Ser. No. 25,236, Mar. 29, 1979, abandoned.

[51] Int. Cl.³ .................. A61K 31/71; C07H 15/22
[52] U.S. Cl. .................................. 424/180; 424/181; 536/16.1
[58] Field of Search ..................... 536/17 R, 17 B

[56] References Cited

U.S. PATENT DOCUMENTS 4,091,032  5/1978  Tadanier et al. ............... 536/17 R
4,169,198  9/1979  Martin et al. .................. 536/17 R Primary Examiner—Johnnie R. Brown
Attorney, Agent, or Firm—Gildo E. Fato; Robert L. Niblack

[57] ABSTRACT

What is described is 2-epi-fortimicin A, 2-epi-fortimicin B or a 2-epi-fortimicin B derivative represented by the formula:

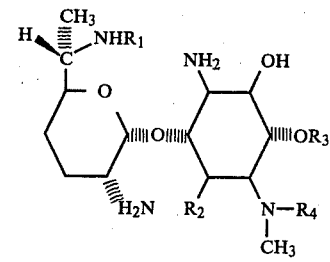

wherein $R_1$ is hydrogen or loweralkyl; $R_2$ is hydrogen or hydroxy; $R_3$ is methyl or hydrogen; and $R_4$ is selected from the group consisting of hydrogen, loweralkyl, aminoloweralkyl, diaminoloweralkyl, N-loweralkylaminoalkyl, N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, acyl of the formula

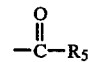

wherein $R_5$ is loweralkyl, aminoacyl, diaminoacyl, hydroxyacyl, N-loweralkylaminoacyl, N,N-diloweralkylaminoacyl, hydroxy-substituted aminoacyl or an amino acid residue other than those defined above and the pharmaceutically acceptable salts thereof useful in the treatment of infections.

41 Claims, No Drawings

2-EPI-FORTIMICIN A AND DERIVATIVES

This application is a continuation-in-part of application Ser. No. 25,236, filed Mar. 29, 1979, now abandoned.

BACKGROUND OF THE INVENTION

The antibacterial and pharmacological properties of many naturally produced aminoglycoside antibiotics can be altered by structural modifications. As an example, certain chemical modifications in the gentamicin and kanamycin family of aminoglycoside antibiotics provide structures which are less toxic than the parent antibiotic. Further, in the same series, certain modifications alter the antibacterial spectrum advantageously either by increasing the intrinsic activity or increasing activity against resistant strains.

Once an aminoglycoside antibiotic has been in clinical use for a period of time, resistant microorganisms may develop. In many cases, the resistance is R-factor mediated and is attributed to the ability of the bacteria to enzymatically modify the amino or hydroxyl groups of the aminoglycoside antibiotics. Thus there is also a need for new entities which can be held in reserve to combat strains which have become resistant to treatment by the clinically used antibiotics.

The fortimicins are a relatively new class of aminoglycoside antibiotics. Fortimicin A is disclosed in U.S. Pat. No. 3,976,768 and fortimicin B in U.S. Pat. No. 3,931,400. Chemical modification of the parent fortimicins have been found to either increase the intrinsic activity of fortimicin A or B, reduce the toxicity or provide therapeutic agents which while having about the same activity, or perhaps somewhat weaker activity but are nevertheless useful as reserve antibiotics in the event resistant strains develop after a period of clinical use of one or more of the fortimicins. The 4-N-acyl derivatives of fortimicin B are disclosed in U.S. Pat. No. 4,091,032 as are the 4-N-alkylfortimicin B derivatives. The 3-O-demethylfortimicin A, fortimicin B and derivatives are disclosed in U.S. Pat. No. 4,124,756.

While a number of fortimicin derivatives have been made to date, and valuable therapeutic agents have been identified, it is desirable to identify new fortimicin antibiotics which either have a broader spectrum, less ototoxicity, exhibit oral activity, etc. as well as for agents which can be held in reserve and used to treat infections caused by organisms which become resistant to fortimicin therapy. The present invention provides one such class of compounds, the 2-epi-derivatives of fortimicin A, fortimicin B and fortimicin A and B derivatives.

SUMMARY OF THE INVENTION

The present invention relates to novel fortimicin derivatives and specifically provides 2-epi-derivatives of fortimicin A, fortimicin B, 4-N-acylfortimicin B derivatives and 4-N-alkylfortimicin B derivatives. The fortimicin antibiotics of this invention are useful as broad spectrum antibiotics in treating infections caused by susceptible strains of *Staphylococcus aureus, Enterobacter aerogenes, Escherichia coli, Klebsiella pneumoniae, Providencia stuartii, Pseudomonas aeruginosa, Salmonella typhimurium, Serratia marescens, Shigella sonnei, Proteus rettgeri, Proteus vulgaris* and *Proteus mirabilis.*

Intermediates useful in making the novel antibiotics are also provided as well as pharmaceutical compositions and methods.

DETAILED DESCRIPTION OF THE INVENTION

The present invention concerns 2-epi-fortimicin compounds, in particular 2-epi-fortimicin A, and their preparations. These novel fortimicin compounds differ from the naturally occurring fortimicins in the configuration of the asymmetric carbon atom at the $C_2$ position of the cyclitol ring.

The 2-epi-fortimicin derivatives of this invention are represented by Formula I:

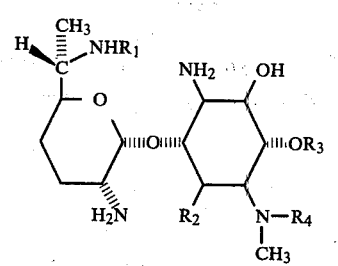

wherein $R_1$ is hydrogen or loweralkyl; $R_2$ is hydrogen or hydroxy; $R_3$ is methyl or hydrogen; and $R_4$ is selected from the group consisting of hydrogen, loweralkyl, aminoloweralkyl; diaminoloweralkyl, N-loweralkylaminoalkyl, N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, acyl of the formula

wherein $R_5$ is loweralkyl, aminoacyl, diaminoloweracyl, hydroxyacyl, N-loweralkylaminoacyl, N,N-diloweralkylaminoacyl, hydroxysubstituted amino acyl or an amino acid residue other than those defined above; and the pharmaceutically acceptable salts thereof.

The intermediates are represented by the formulas:

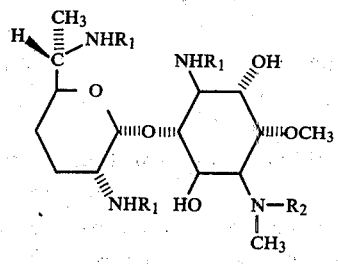

wherein $R_1$ is hydrogen, monocyclicaryloxycarbonyl or acetyl; and $R_2$ is carboethoxy.

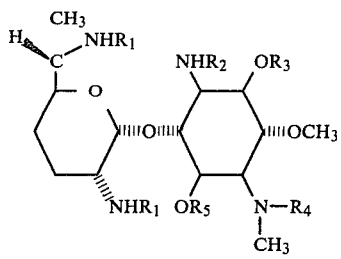

wherein $R_1$ is hydrogen, monocyclicaryloxycarbonyl, acyl of the formula

wherein Y is loweralkyl, or loweralkyl; $R_2$ is hydrogen, monocyclicaryloxycarbonyl or acyl of the formula

$R_3$ is hydrogen, N-benzyloxycarbonylglycyl, glycyl, benzyl or substituted benzyl; $R_4$ is hydrogen, N-benzyloxycarbonylglycyl or glycyl; $R_5$ is hydrogen, $R_2$ and $R_3$ when taken together form a cyclic benzyloxyoxazoline, a cyclic carbamate or a cyclic methyloxazoline moiety; $R_2$ and $R_4$ when taken together form a cyclic urea moiety; and $R_4$ and $R_5$ when taken together form a cyclic carbamate moiety.

The term "loweralkyl", as used herein, refers to straight or branched chain alkyl radicals having from 1 to 7 carbon atoms, including, but not limited to methyl, ethyl, n-propyl, iso-propyl, n-butyl, sec-butyl, tert-butyl, n-pentyl, 2-methylbutyl, 2,2-dimethylpropyl, n-hexyl, 2,2-dimethylbutyl, 1-methylpentyl, 2-methylpentyl, n-heptyl and the like.

The term "acyl" as used in the definition in the specification and claims, refers to acyl groups represented by the formula

wherein $R_3$ is loweralkyl, i.e., acetyl, propionyl, butyryl, valeryl and the like.

The terms "aminoacyl" et seq. for $R_4$ include the naturally occurring aminoacids such as glycyl, valyl, alanyl, sarcosyl, leucyl, isoleucyl, prolyl, seryl, and the like as well as groups such as 2-hydroxy-4-aminobutyryl. The aminoacids residues included in the above terms can be in the L- or D- configurations or a mixture thereof, with the exception of course of glycyl.

The term "monocyclicaryloxycarbonyl" as used herein refers to protecting groups such as benzyloxycarbonyl, paramethylbenzyloxycarbonyl, paramethoxybenzyloxycarbonyl or orthonitrobenzyloxycarbonyl which are commonly used as N-protecting groups in peptide synthesis and in other areas where N-protection is required.

The term "substituted benzyl" as used herein refers to benzyl substituted by for example, alkyl, alkoxy, nitro or halo such as p-methyl, p-methoxy, o-nitro, p-chloro or p-bromo.

The term "pharmaceutically acceptable salts", as used herein, refers to the non-toxic acid addition salts of the compounds of this invention which can be prepared in situ during the final isolation and purification or by separately reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartarate, napsylate and the like. It will be apparent to those skilled in the art that, depending upon the number of available amino groups for salt formation, the salts of this invention can be per-N-salts.

The compounds of Formula I, are useful as broad spectrum antibiotics when administered parenterally to a patient suffering from an infection caused by a susceptible strain of bacilli in dosages of from 10 to 100 mg/kg of body weight daily, based on lean body weight as is good medical practice with the aminoglycoside antibiotics, and preferably from about 15 to about 30 mg/kg of body weight daily. The compounds are preferably administered in divided doses, i.e. three to four times daily and can be administered by intravenous, intramuscular, intraperitoneal, or subcutaneous routes of administration for systemic activity and orally to sterilize the intestinal tract. The antibiotics of this invention can also be administered in suppository form.

The antibiotics of Formula I can be used as described above in the treatment of infections caused by susceptible strains of organisms such as *Staphylococcus aureus, Enterobacter aerogenes, Escherichia coli, Klebsiella pneumoniae, Providencia stuartii, Pseudomonas aeruginosa, Salmonella typhimurium, Shigella sonnei, Proteus rittgeri, Proteus vulgaris* and *Proteus mirabilis.*

The term "susceptible strains" refers to strains of bacilli which have been demonstrated to be sensitive to a particular antibiotic in a standard in vitro sensitivity test and thus in vitro activity has been established for a particular antibiotic against a specific strain of a specific organism.

The compounds of Formula I can also be incorporated into scrub solutions for sterilizing surfaces such as laboratory benchtops, operating room surfaces and the like.

The following reaction scheme is illustrative of processes for making compounds of this invention.

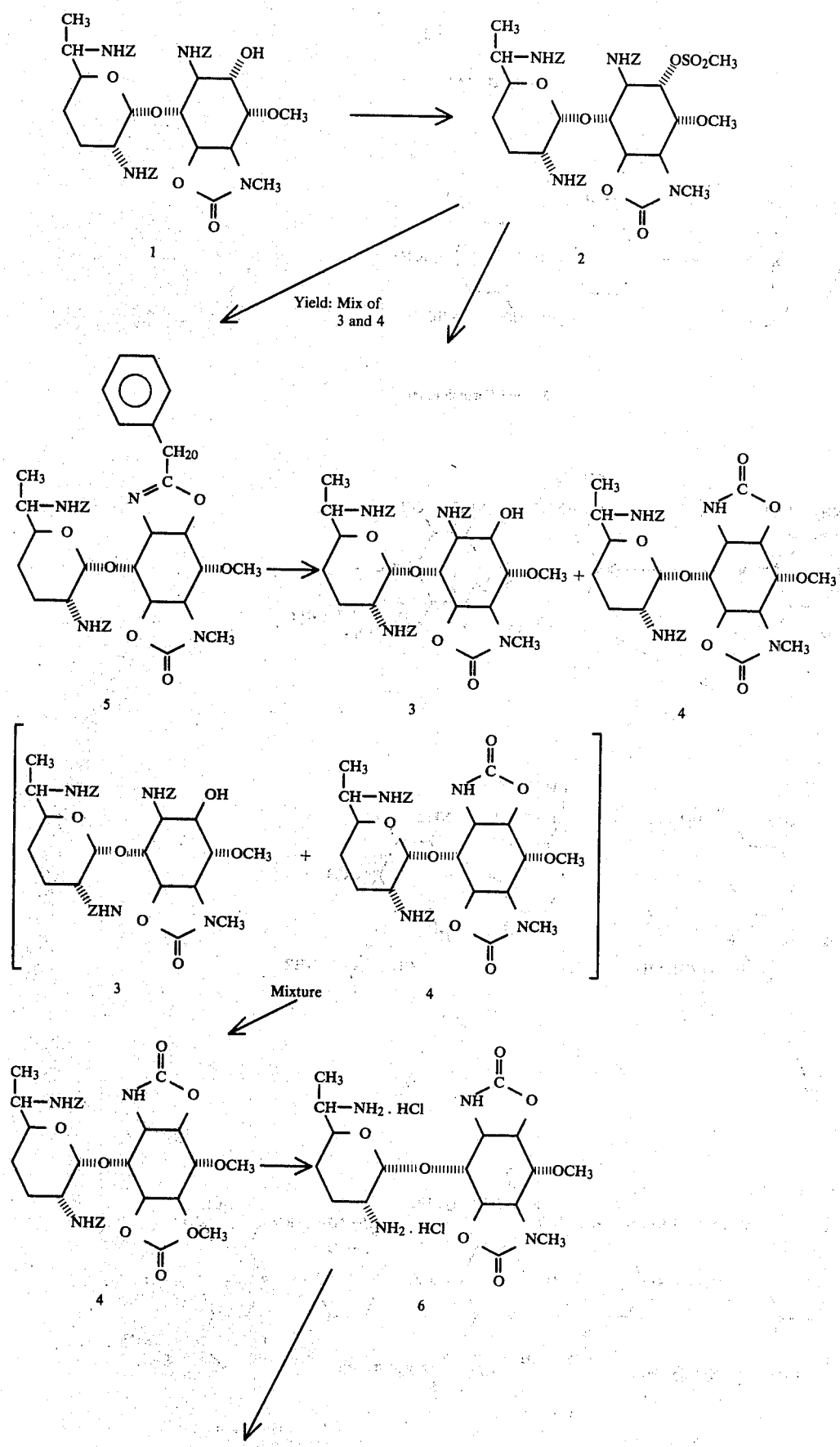

-continued
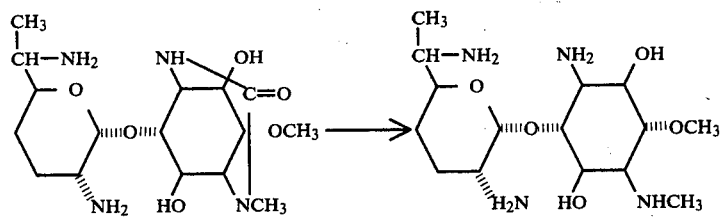
7          8 (2-epi-Fortimicin B)
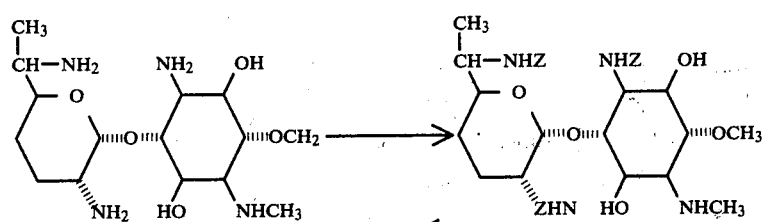
8          9
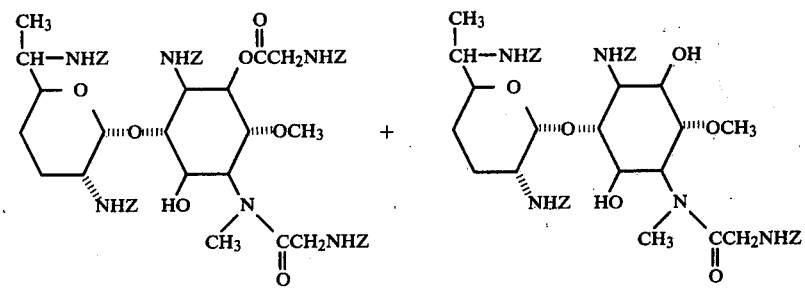
10          11
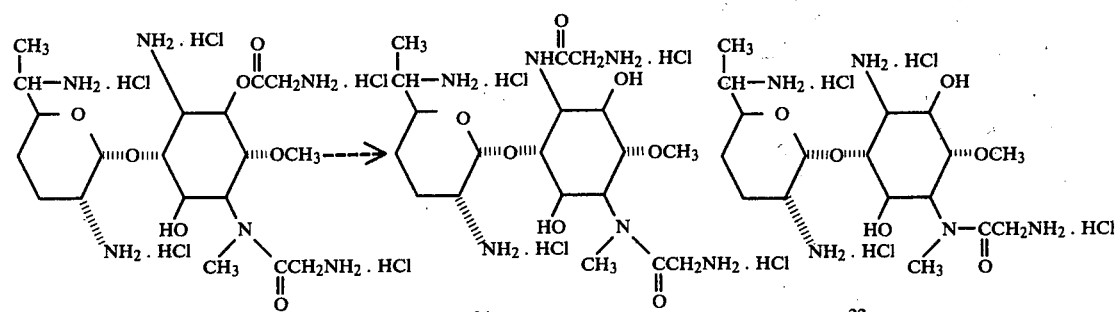
23          24          22
2-epi-Fortimicin A
Tetrahydrochloride -continued
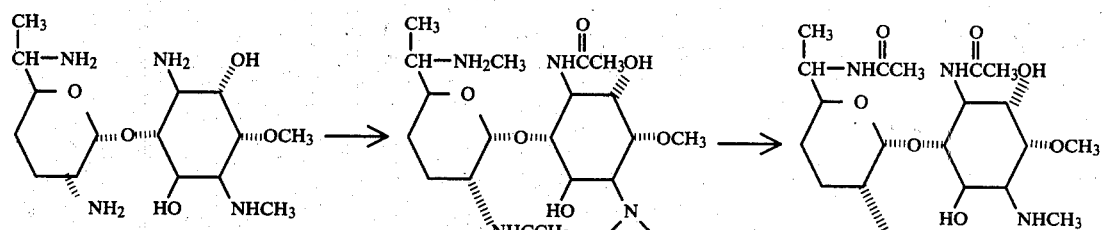
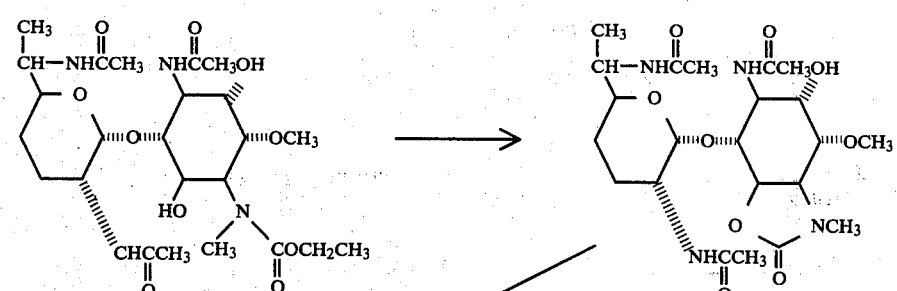
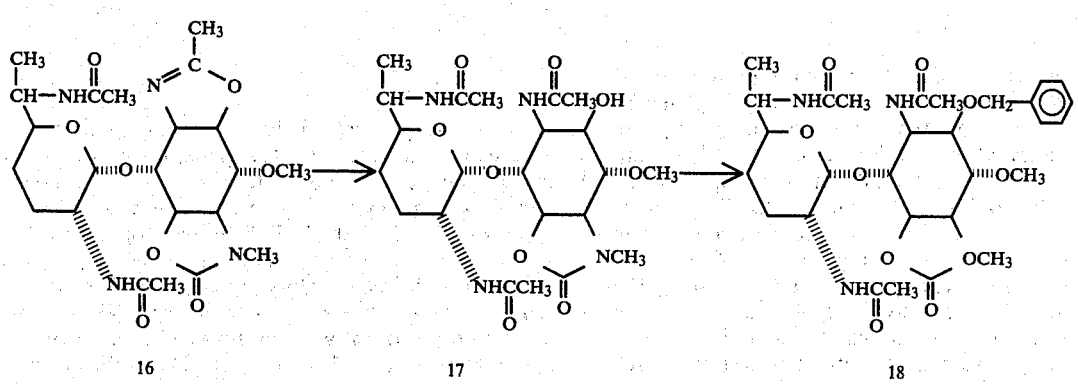
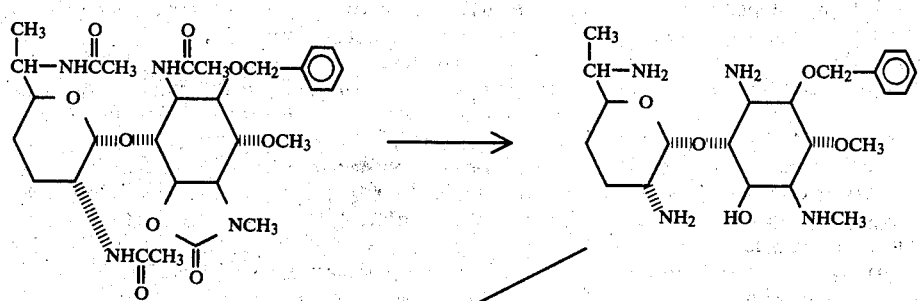

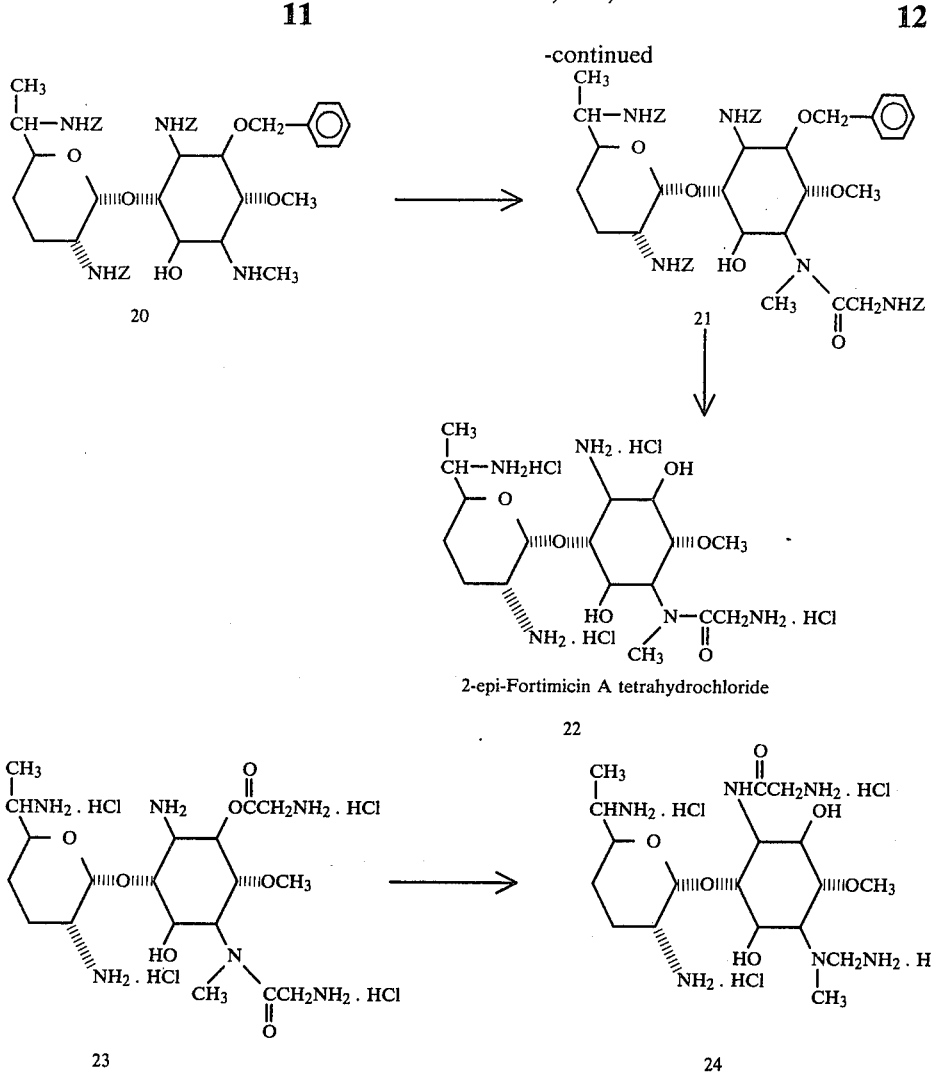

Two processes are described for the preparation of 2-epi-fortimicin compounds. In the first, 1,2',6'-tri-N-benzyloxycarbonylfortimicin B, 4,5-carbamate (1) prepared as described in U.S. Pat. No. 4,091,032 is converted to the 2-O-methanesulfonate (2). Solvolysis of the 2-O-methanesulfonate in aqueous 1,2-dimethoxyethane in the presence of ammonium acetate acetate gives an approximately equimolar mixture of the tri-N-benzyloxycarbonyl-2-epi-4,5-carbamate (3) and the 2',6'-di-N-benzyloxycarbonyl 2-epi-biscarbamate (4). Alternately when the solvolysis of 2-O-methanesulfonate is carried out in a mixture with aqueous tetrahydrofuran and sodium bicarbonate the 2-epi-oxazoline (5) is formed. When the latter (5) is heated under reflux in a solution prepared from ammonium acetate and aqueous 1,2-dimethoxyethane an approximately equimolar mixture of the 2-epi-4,5-carbamate (3) and the 2-epi-biscarbamate (4) is formed.

It should be noted that the desired C2-epimerization occurs on solvolysis of the 2-O-methanesulfonate (2). When the solvolysis is carried out in aqueous 1,2-dimethoxyethane in the presence of ammonium acetate, the products are the 2-epi mono and biscarbamates (3) and (4). When the solvolysis is carried in in aqueous tetrahydrofuran the product is the 2-epi oxazoline (5).

The mixture of the 2-epi mono and biscarbamates (3) and (4) may be separated into the pure components by chromatography. Alternately when the mixture of 2-epi mono and biscarbamates is heated under reflux with a mixture of sodium bicarbonate and methanol, then 2-epi monocarbamate (3) is converted to the 2epi biscarbamate (4) which may be isolated by chromatography.

Hydrogenolysis of the 2',6'-di-N-benzyloxycarbonyl-2-epi biscarbamate (4) with 5% Pd/C in the presence of 0.2 N methanolic hydrochloric acid gives 2-epi-fortimycin B-1,2,4,5-biscarbamate dihydrochloride (6). Incomplete hydrolysis of (6) with aqueous sodium hydroxide gives a mixture of the 2-epi-1,4 urea (7) and the desired 2-epi fortimicin B (8). Complete hydrolysis of (6) to (8) is effected by employing a longer hydrolysis time to give exclusively 2-epi-fortimicin B (8).

2-epi-Fortimicin B (8) is converted to 1,2',6'-tri-N-benzyloxycarbonyl fortimicin B (9) with N-benzyloxycarbonylsuccinimide. Attempted 4-N-acylation of 1,2'6'-etc (9) with the N-hydroxysuccinimide ester of N-benzyloxycarbonylglycine to form tetra-N-benzyloxycarbonyl-2-epi-fortimicin A (11) gives instead tetra-N-benzylocycarbonyl-2-O-[N-benzyloxycarbonylglycyl]-2-epi-fortimicin A (10) as the major product. The desired tetra-N-benzyloxycarbonyl-2-epi-fortimicin A (11) was the minor product.

Catalytic hydrogenations of (10) and (11) with 5% Pd/C in 0.2 N methanolic hydrochloric acid give 2-O-glycyl-2-epi-fortimicin A (23) and 2-epi-fortimicin A

(22) respectively, isolated as their perhydrochloride salts.

Treatment of an aqueous solution of 2-O-glycyl-2-epi-fortimicin A pentahydrochloride (23) with excess AG2-X8 (011) resin followed by treatment with excess hydrochloric acid gave 1-N-glycyl-2-epi-fortimicin A pentahydrochloride (24).

Since the diacylated product (10) was the principle product obtained even when only one equivalent of the N-hydroxysuccinimide ester of N-benxzyloxycarbonylglycine was employed, an alternate synthesis of 2-epi-fortimicin A was devised in which the C-2 hydroxyl group is protected by a benzyl group during the critical 4-N-acylation step. The benzyl group is the protecting group of choice since it is readily removed during the hydrogenolysis step which removes N-protecting benzyloxycarbonyl groups. The alternate synthesis is accomplished in the following manner.

Fortimicin B is converted to tetra-N-acetylfortimicin B (12). Selective hydrolysis of (12) with sodium bicarbonate in acqeous methanol gives 1,2',6'-tri-N-acetyl-fortimicin B (13). The latter is converted to the 4-N-ethoxycarbonyl derivative (14) which is readily cyclized to the 4,5-carbonate (15) in a refluxing suspension of sodium bicarbonate in aqueous methanol. Treatment of (15) with methanesulfonic anhydride in pyridine gives the 2-epi-1,2-oxazoline (16) which is probably formed via the intermediate 2-O-methanesulfonic (15a). Formation of the oxazoline occurs with the desired epimerization at the $C_2$ position. Hydrolysis of (16) with aqueous hydrochloric acid in tetrahydrofuran gives 1,2',6'-tri-N-acetyl-2-epi-fortimicin B, 4,5-carbamate (17). The latter, is converted to the 2-O-benzyl ether (18) with benzylbromide in N,N-dimethylformamide in the presence of barium oxide and barium hydroxide. Hydrolysis of (18) with aqueous sodium hydroxide gives 2-O-benzyl-2-epi-fortimicin B (19). Treatment of (19) with N-benzyloxycarbonyloxysuccinimide gives 1,2',6'-tri-N-benzyloxycarbonyl-2-O-benzyl-2-epi for-timicin B (20). Treatment of the latter with the N-hydroxysuccinimide ester of N-benzyloxycarbonylglycine gives tetra-N-benzyloxycarbonyl-2-O-benzyl-2-epi-fortimicin A (2). Catalytic hydrogenolysis of (21) in 0.2.N. hydrochloric acid in the presence of 5% Pd/C gives 2-epi-fortimicin A as the tetrahydrochloride salt (22); identical with that prepared from tetra-N-benzyloxycarbonyl-2-epi-fortimicin A (11) as described above.

EXAMPLE 1

1,2',6'-Tri-N-benzyloxycarbonyl-2-O-methanesulfonyl-fortimicin B 4,5-carbamate (2)

To a magnetically stirred solution of 0.155 g. of 1,2',6'-tri-N-benzyloxycarbonyl fortimicin B 4,5-carbamate (1) in 2 ml. of pyridine, cooled in an ice bath, is added 0.42 g. of methanesulfonic anhydride. Stirring is continued with cooling for 1 hour and then at ambient temperature overnight. The resulting mixture is poured into 100 ml. of 5% aqueous NaHCO$_3$. The aqueous suspension is extracted twice with 50 ml. portions of CHCl$_3$. The CHCl$_3$ solutions are combined and washed with 100 ml. of 5% aqueous NaHCO$_3$. The CHCl$_3$ solution is dried over anhydrous MgSO$_4$ Evaporation of the CHCl under reduced pressure leaves 0.169 of (2) as a glass: $[\alpha]_D^{21} -4.24°$ (c 1%, CH$_3$OH); i.r. (CDCl$_3$) 3440, 3300, 1760, 1708 cm$^{-1}$; NMR (CDCl$_3$) δ1.00 d (J 3.6 Hz, C$_6'$-CH$_3$); 2.83 (NCH$_3$); 2.99 (OSO$_2$CH$_3$); 3.52 (OCH$_3$).

Anal. Calcd for C$_{41}$H$_{50}$N$_4$O$_{14}$:C, 57.60; H, 5.90; N, 6.55. Found: C, 58.79, H, 6.28; N, 7.12.

EXAMPLE 2

2',6'-Di-N-benzyloxycarbonyl-2-epi-fortimicin B 1,2-[2-benzyloxy]oxazoline 4,5-carbamate (5)

A magnetically stirred mixture of 2.0 g. of 1,2,6'-tri-N-benzyloxycarbonyl-2-O-methanesulfonylfortimicin B 4,5-carbamate (2) 1.22 g. of sodium bicarbonate, 7.4 ml. of water and 29.6 ml. of tetrahydrofuran is heated at 67 degrees for 5 days. The resulting mixture is poured into 500 ml. of 5% aqueous NaHCO$_3$. The aqueous suspension is extracted with 250-ml. portions of CHCl$_3$. The CHCl solutions are combined and dried (MgSO$_4$). Evaporation of the CHCl left 1.77 g. of a light yellow glass: $[\alpha]_D^{23} +6°$ (C1%, CH$_3$OH); i.r. (CDCl$_3$) 3444, 3327, 1759, 1711, 1665 cm$^{-1}$; NMR (CDCl$_3$) δ1.19 d (J=6.6 Hz) (C$_6'$-CH$_3$), 2.92 (NCH$_3$), 3.47 (OCH$_3$).

EXAMPLE 3A 1,2',6'-Tri-N-benzyloxycarbonyl-2-epi-fortimicin B 4,5-carbamate (3) and 2',6'-di-N-benzyloxycarbonyl-2-epi-fortimicin B 1,2;4,5-biscarbamate (4)

A magnetically stirred solution of 0.427 g. of 1,2',6'-tri-N-benzyloxycarbonyl-2-O-methanesulfonylfortimicin B 4,5-carbamate (2), 0.116 g. of ammonium acetate, 3 ml. of water, and 6 ml. of 1,2-dimethoxyethane is heated under reflux for 21 hours. The resulting solution is cooled and poured into 100 ml. of 5% aqueous NaHCO$_3$. The aqueous suspension is extracted twice with 50 ml. portions of CHCl$_3$. The CHCl$_3$ extracts are combined and dried over anhydrous magnesium sulfate. Evaporation of the CHCl$_3$ under reduced pressure leaves 0.386 mg. of a mixture of (3) and (4).

A sample of 3.01 g. of the mixture of (3) and (4), prepared as described above was chromatographed on a column of 250 g. of silica gel packed and eluted with a solvent system composed of ethyl acetate, 1,2-dichloroethane [9:1 (v/v)]. Initial fractions gave 1.24 g. of 1,2',6'-tri-N-benzyloxycarbonyl-2-epi-fortimicin B 4,5-carbamate (3):

$[\alpha]_D^{21} +8.5°$ (c 1%, CH$_3$OH); i.r. (CDCl$_3$) 3442, 3328 (shoulder), 1743, 1698 cm$^{-1}$; NMR (CDCl$_3$) 1.05 d (J=6.2 Hz, C$_6'$-CH$_3$); 2.83 (NCH$_3$); 3.43 (OCH$_3$).

Anal. Calcd for C$_{40}$H$_{48}$N$_4$O$_{12}$:C, 61.48; H, 6.23; N, 7.21. Found: C, 61.64; H, 6.37; N, 7.25.

Further elution of the column gave 0.965 g. of 2',6'-di-N-benzyloxycarbonyl-2-epi-fortimicin B 1,2;4,5-biscarbamate (4):

$[\alpha]_D^{21} +7.3°$ (c 1%, CH$_3$OH); i.r. (CDCl$_3$) 3443, 3323, 1749, 1699 cm$^{-1}$; NMR (CDCl$_3$) δ1.17 d (J 6.8 Hz, C$_6'$-CH$_3$), 2.94 (NCH$_3$), 3.52 (OCH$_3$).

Anal. Calcd for C$_{33}$H$_{41}$N$_4$O$_{11}$:C, 59.18; H, 6.17; N, 8.37. Found: C, 59.50; H, 6.06; N, 8.09.

EXAMPLE 3B

A solution of 1.5 g. 2',6'-di-N-benzyloxycarbonyl-2-epi-fortimicin B-1,2-[2-benzyloxy] oxazoline 4,5-carbamate (5), 0.435 g. of ammonium acetate, 11.3 ml of water and 22.6 mg of 1,2-dimethoxyethane is heated under reflux for 3 hours. A similar reaction is carried out with 0.100 g of (5), 0.029 g of ammonium acetate, 0.75 ml of water and 1.5 ml of 1,2-dimethoxyethane. The two reaction solutions are combined and shaken with a mixture of 500 ml of 5% aqueous and 250 ml of CHCl$_3$. The CHCl$_3$ solutions are combined and dried (MgSO$_4$). Evaporation of the CHCl$_3$ under reduced pressure leaves 1.46 g of a glass. The latter is chromatographed on a column of 150 g. of silica gel packed and eluted with a solvent system composed of ethyl acetate-1,2-dichloroethane [1:1(v/v)] to yield 0.583 g. of 1,2',6'-tri-N-benzyloxycarbonyl-2-epi-fortimicin B-4,5-carbamate (3) and 0.153 g. of 2',6'-di-N-benzyloxycarbonyl-2-epi-fortimicin B-1,2;4,5-biscarbamate (4). The products (3) and (4) are identical with those prepared directly from the methanesulfonate (2) with ammonium acetate in aqueous 1,2-dimethoxyethane as described above.

In addition 0.256 g of a mixture of (4) and a more polar product (1:1 mixture by TLC) is isolated from later chromatography fractions.

EXAMPLE 4

2',6'-Di-N-benzyloxycarbonyl-2-epi-fortimicin B 1,2;4,5-biscarbamate (4)

A magnetically stirred solution of 13.0 g. of a mixture of 1,2',6'-tri-N-benzyloxycarbonyl-2-epi-fortimicin B 1,2-carbamate (3) and 2',6'-di-N-benzyloxycarbonylfortimicin B 1,2;4,5-biscarbamate prepared from the methanesulfonate (2) as described in Example 3A (4), 8.0 g. of NaHCO$_3$, and 350 ml. of CH$_3$OH is heated under under reflux overnight. The resulting solution is cooled, and shaken with a mixture of CHCl$_3$ and 5% aqueous NaHCO$_3$. The CHCl$_3$ solution is separated and dried over anhydrous magnesium sulfate. Evaporation of the CHCl$_3$ under reduced pressure leaves 13.0 g. of (4) identical with that described in Example 2.

EXAMPLE 5

2-epi-Fortimicin B 1,2;4,5-biscarbamate dihydrochloride (6)

2',6'-Di-N-benzyloxycarbonylfortimicin B 1,2;4,5-biscarbamate (1.0 g., 4) in 30 ml. of 0.4 N-hydrochloric acid in methanol is hydrogenated for 4 hours under 3 atmospheres of hydrogen in the presence of 1 g. of 5% Pd on carbon. The catalyst is removed by filtration and the solvent is evaporated under reduced pressure. Residual hydrochloric acid is removed by codistillation with methanol under reduced pressure leaving 0.717 g. of (6) as a white glass:

$[\alpha]_D^{22}+36°$ (c 1%, CH$_3$OH); i.r. (KBr) 1738, 1723 cm$^{-1}$; NMR (D$_2$O) δ1.79 d (J C$_6'$-CH$_3$), 3.42 (NCH$_3$), 4.04 (OCH$_3$), 5.56 d (J=3.6 HZ, C$_1'$-H);

MS: M+ Calcd for C$_{17}$H$_{28}$N$_4$O$_7$: 400.1958. Meas. 400.1933

EXAMPLE 6

2-epi-Fortimicin B (8) and 2-epi-Fortimicin B 1,4-urea (7)

A solution of 0.680 g. of 2-epi-fortimicin B 1,2;4,5-biscarbamate dihydrochloride (6) in 80 ml. of 1 N aqueous sodium hydroxide is heated at 75 degrees for 24 hours. The resulting solution is brought to pH 7 by addition of 1 N-hydrochloric acid and then evaporated to dryness under reduced pressure. Residual water is removed by codistillation with ethanol. To the residue is added 100 ml. of ethanol, and the resulting suspension is briefly heated to boiling, cooled, and filtered. The insoluble residue is washed thoroughly with ethanol, and the ethanol solutions are combined. The ethanol is evaporated leaving 0.550 g. of light yellow glass. This material is chromatographed on a column of 40 g. of silica gel prepared and eluted with a solvent system prepared from the lower phase of a mixture of chloroform-methanol-ammonium hydroxide (concentrated)-water [2:2:1:1 (v/v/v/v)]. Early fractions gave 160 mg. of 2-epi-fortimicin B (8), identical with that prepared as described in Example 7.

Further elution gives 88 mg. of fortimicin B 1,4-urea (7):

$[\alpha]_D^{22}+12.3°$ (C 1%, CH$_3$OH); NMR (D$_2$O) δ1.48 (J=6.6 Hz C$_6'$-CH$_3$), 3.50 (NCH$_3$); 3.96 (OCH$_3$); 5.46 d (J=3.4 Hz, C$_1'$-H).

MS: M+ Calcd for C$_{16}$H$_{30}$N$_4$O$_6$: 374.2165. Meas. 374.2193.

Diaminosugar calcd for C$_7$H$_{15}$N$_2$O: 143.1184. Meas. 143.1173.

Cyclitol calcd for C$_9$H$_{15}$N$_2$O$_4$: 215.1032. Meas. 215.1035.

EXAMPLE 7

2-epi-Fortimicin B (8)

A solution of 4.94 g. of 2-epi-fortimicin B 1,2;4,5-biscarbamate dihydrochloride (6) in 500 ml. of 1 N aqueous sodium hydroxide is heated at 75 degrees for 66 hours. The resulting solution is cooled, brought to pH 7 with 1 N hydrochloric acid and evaporated to dryness under reduced pressure. The residue is treated with several portions of boiling ethanol, and the resulting suspension filtered. Evaporation of the ethanol leaves 4.12 g. of glass. The product is chromatographed on a column of 450 g. of silica gel packed and eluted with a solvent system composed of chloroforml-methanol-ammonium hydroxide (concentrated)-water [10:10:1:1 (v/v/v/v)] to yield of 3.0 g. of 2-epi-fortimicin B (8):

$[\alpha]_D^{23}+77.8°$ (c 1%, CH$_3$OH); NMR (D$_2$O) δ1.50 d (J=6.8 Hz, C$_6'$-CH$_3$); 2.83 (NCH$_3$); 3.99 (OCH$_3$) 5.38 d (J=3.4 Hz, C$_1'$-H);

MS M+ Calcd for C$_{15}$H$_{32}$N$_4$O$_5$: 348.2373. Meas. 348.2391.

EXAMPLE 8

1,2',6'-Tri-N-benzyloxycarbonyl-2-epi-fortimicin B (9)

To a magnetically stirred solution of 2.9 g. of 2-epi-fortimicin B (8), 42 ml. of water, and 84 ml. of methanol, cooled in an ice bath, is added 6.4 g. of N-benzyloxycarbonyloxysuccinimide. Stirring is continued with cooling for 3 hours and then at ambient temperature overnight. The resulting solution is shaken with a mixture of CHCl$_3$ and 5% aqueous NaHCO$_3$. The CHCl$_3$ solution is separated and the aqueous solution is extracted with two portions of CHCl$_3$. The CHCl$_3$ solutions are combined and dried (MgSO$_4$). Evaporation of CHCl$_3$ under reduced pressure leaves 6.91 g. of a glass which is chromatographed on a column of 450 g. of silica gel packed and eluted with a solvent system composed of 1,2-dichloroethane-ethanol [9:1 (v/v)] to yield 3.1 g. of 1,2',6'-tri-N-benzyloxycarbonyl-2-epi-fortimicin B (9);

$[\alpha]_D^{23.2}+59°$ (c 1%, CH$_3$OH), i.r. (CDCl$_3$) 3440, 3330, 1708 cm$^{-1}$; NMR (CDCl$_3$) δ1.045 d (J=7.0 HZ, C$_6'$-CH$_3$), 2.40 (NCH$_3$), 3.39 (OCH$_3$).

Anal. Calcd for C$_{39}$H$_{50}$N$_4$O$_{11}$:C, 62.38; H, 6.71; N, 7.46. Found: C, 62.11; H, 6.79; N, 7.36.

EXAMPLE 9

Tetra-N-benzyloxycarbonyl-2-O-[N-benzyloxycarbonylglycyl]-2-epi-fortimicin A (10) and Tetra-N-benzyloxycarbonyl-2-epi-fortimicin A (11)

A solution of 1.2 g. of 1,2',6'-tri-N-benzyloxycarbonyl-2-epi-fortimicin B (9), 1.24 g. of N-(N-benzyloxycarbonylglycyloxy)succinimide and 90 ml. of tetrahydrofuran is allowed to stand at room temperature for three days. The resulting ing solution is shaken with a mixture of 5% aqueous NaHCO$_3$ and CHCl$_3$. The CHCl$_3$ solution is separated, and the aqueous solution is extracted twice with CHCl. The CHCl$_3$ solutions are combined and dried (MgSO$_4$). The product is chromatographed on a column of 200 g. of silica gel packed and eluted with a solvent system composed of 1,2-dichloroethane-ethanol-water [19:1:0.1 (v/v/v/)]. Earlier fractions give 1.17 g. of tetra-N-benzyloxycarbonyl-2-O-[N-benzyloxycarbonylglycyl]-2-epi-fortimicin A (10):

$[\alpha]_D^{23} +21.9°$ (c 1%, CH$_3$OH); i.r. (CHCl$_3$) 3432; 1752 (shoulder), 1712, 1638 cm$^{-1}$. NMR (CDCl$_3$) $\delta$1.16 d (J 7 Hz, C$_6'$-CH$_3$); 2.85, 3.0 [rotamers, N(CH$_3$)]; 3.33 (OCH$_3$).

Anal. Calcd for C$_{59}$H$_{68}$N$_6$O$_{17}$:C, 62.53; H, 6.05; N, 7.41. Found: C, 62.40; H, 6.05; N, 7.34.

Further elution of the column gives 222 mg. of tetra-N-benzyloxycarbonyl-2-epi-fortimicin A (11): $[\alpha]_D^{22} +43°$ (c 1%, CH$_3$OH), i.r. (CDCl$_3$) 3436, 1710, 1635 cm$^{-1}$; NMR (CDCl$_3$) $\delta$1.15 d (J=6.5 Hz, C$_6'$-CH$_3$); 2.87, 3.04 [rotamers, NCH$_3$]; 3.48 (OCH$_3$).

Anal. Calcd for C$_{49}$H$_{59}$N$_5$O$_{14}$:C, 62.47; H, 6.31; N, 7.47. Found: C, 62.67; H, 6.55; N, 7.26.

EXAMPLE 10

1,2',6'-Tri-N-acetylfortimicin B (13)

A magnetically stirred mixture of 33.4 g of tetra-N-acetylfortimicin B (12) (R. S. Egan, R. S. Stanaszek, M. Cirovic, S. L. Mueller, J. Tadanier, J. R. Martin, P. Collum, A. W. Goldstein, R. L. DeVault, A. C. Sinclair, E. E. Fager and L. A. Mitschner, J. Antibiotics), No. 7, 552 (1977) 20 g of NaHCO$_3$ 300 ml. of water, and 1 liter of CH$_3$OH is heated under reflux overnight. The major portion of the solvent is evaporated under reduced pressure, and residual water is removed by codistillation with several portions of ethanol under reduced pressure. The residue is triturated with several portion of warm CHCl$_3$. The supernatant is filtered and evaporated to dryness under reduced pressure leaving 29.1 g. of crude 1,2',6'-tri-N-acetylfortimicin B (13).

A sample (5.13 g.) of (13) thus prepared is chromatographed on a column of 400 g. of silica gel, packed and eluted with a solvent system composed of chloroform-95% aqueous methanol-ammonium hydroxide (concentrated) [18:6:0.5 (v/v/v)] to yield 4.37 g. of pure 1,2',6'-tri-N-acetylfortimicin B (13).

$[\alpha]_D^{21.2} +27.8°$ (c 1%, CH$_3$OH); i.r. (CDCl$_3$) 3553, 3439, 3333, 1655 cm$^{-1}$; NMR (CDCl$_3$) $\delta$1.16 d (J=6.2 Hz, C$_6'$-CH$_3$); 1.94, 1.98, 1.99 (OCOCH$_3$'s); 2.41 (NCH$_3$); 3.45 (OCH$_3$); 5.2 d (J=3 Hz, C$_{1'}$-H).

MS M$^+$ Calcd for C$_{21}$H$_{38}$N$_4$O$_8$: 474.2690. Meas. 474.2685.

EXAMPLE 11

1,2',6'-Tri-N-acetyl-4-N-ethoxycarbonylfortimicin B (14)

A magnetically stirred solution of 0.6128 g. of 1,2',6'-tri-N-acetylfortimicin B (13), 0.270 ml. of ethyl chloroformate and 30 ml. of CH$_3$OH is stirred at room temperature for 4.5 hours. Solid NaHCO$_3$ (0.4271 g.) is added and stirring is continued for 1 hour. The resulting suspension is filtered, and the filtrate is evaporated to dryness under reduced pressure. The residue is washed with CHCl$_3$, and the supernatant is filtered and evaporated to dryness leaving 628.8 mg of white glass. The latter is chromatographed on a column of 60 g. of silica gel packed and eluted with a solvent system composed of chloroform-methanol [9:1 (v/v)] to yield 378.4 mg. of 1,2',6'-tri-N-acetyl-4-N-ethoxycarbonylfortimicin B (14):

i.r. (CDCl$_3$) 3537, 3337, 1657 cm$^{-1}$. NMR (CDCl$_3$) $\delta$1.15 d (J=6.4 Hz, C$_6'$-CH$_3$), 1.27 t (J=7.7 Hz, OCH$_2$CH$_3$), 1.97, 1.98, 1.99 (OCOCH$_3$'s), 3.02 (NCH$_3$), 3.42 (OCH$_3$).

EXAMPLE 12

1,2',6'-Tri-N-acetylfortimicin B 4,5-carbamate (15)

A. A solution prepared from 0.3473 of 1,2',6'-tri-N-acetyl-4-N-ethoxycarbonylfortimicin B (14), 0.4184 g. of 1,5-diazabicyclo[5.4.0]undecene-5 and 20 ml. of benzene is heated under reflux for five days. The benzene is evaporated and the residue is chromatographed on a column of 60 g. of silica gel packed and eluted with a solvent system composed of chloroform-methanol [87:13 (v/v)] to yield 0.2792 g. of 1,2',6'-tri-N-acetylfortimicin B 4,5-carbamate (15), identical with that prepared as described below.

1,2',6'-Tri-N-acetylfortimicin B 4,5-carbamate (15)

B. To a magnetically stirred suspension of 29.1 g. of crude 1,2',6'-tri-N-acetylfortimicin B (13), prepared as described above, 21 g. of NaHCO$_3$, and 1.4 l of CH$_3$OH is added dropwise to 14 ml. of ethyl chloroformate. The resulting suspension is stirred overnight at room temperature, and then heated under reflux for 1.5 hours. The CH$_3$OH is evaporated under reduced pressure, and the residue is triturated with CHCl$_3$. The supernatant is filtered and the CHCl$_3$ is evaporated leaving 30.9 g. of glass. The latter is chromatographed on a column of 750 g. of silica gel packed and eluted with a solvent system composed of 1,2'-dichloroethane-methanol $[\alpha]_D^{21.2} +4.8°$ (c 1%, CH$_3$OH), i.r. (CDCl$_3$) 3552, 3440, 3402, 3315, 1753, 1658 cm$^{-1}$, NMR (CDCl$_3$) 1.18 d (J=7.0 Hz, C$_6'$-CH$_3$); 2.00 (3H), 2.04 (6H) (NHCOCH$_3$'s); 2.91 (NCH$_3$); 3.48 (OCH$_3$); 4.88 d (J=3 Hz, Cl'-H).

EXAMPLE 13

2',6'-Di-N-acetyl-2-epi-fortimicin B 1,2-[2-methyl]oxazoline 4,5-carbamate (16)

To a magnetically stirred solution of 5.09 g. of 1,2',6'-tri-N-acetylfortimicin B 4,5-carbamate (15) in 50 ml. of pyridine, cooled in an ice bath, is added 3.50 g. of methanesulfonic anhydride. Stirring is continued with cooling for 1 hour, and then at ambient temperature overnight. The resulting mixture is shaken with a mixture of 5% aqueous NaHCO$_3$ and CHCl$_3$. The CHCl$_3$ solution is separated, and the aqueous solution is again extracted with CHCl₃. The CHCl₃ solutions are combined and dried (MgSO₄). Evaporation of the CHCl₃ leaves 4.47 g. of 2',6'-di-N-acetyl-2-epi-fortimicin B 1,2-[2-methyl]oxazoline 4,5-carbamate (16):

i.r. (CDCl₃) 3442, 3321, 1746, 1649 cm⁻¹; NMR (CDCl₃) 1.19 d (J=6.2 Hz, C₆'-CH₃); 1.99 (NHCOCH₃'s); 2.04

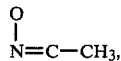

2.97 (NCH₃), 3.56 (OCH₃); MS M⁺ Calcd. for C₂₂H₃₄N₄O₆: 482.2377; Meas. 482.2364; Cyclitol Calcd. for C₁₁H₁₇N₂O₅: 257.1137; Meas. 257.1161; Diaminosugar calcd. for C₁₁H₁₉N₂O₃: 227.1396; Meas. 227.1415.

EXAMPLE 14

1,2',6'-Tri-N-acetyl-2-epi-fortimicin B 4,5-carbamate (17)

A magnetically stirred solution of 4.40 g. of 2',6'-di-N-acetyl-2-epi-fortimicin B 1,2-[2-methyl]oxazoline, 4,5-carbamate (16) 45 ml. of 0.4 N- HCl and 180 ml. of tetrahydrofuran is kept at room temperature for 0.5 hours. Sodium bicarbonate solution (150 ml., 5% aqueous) is added. The major portion of the solvent is evaporated under reduced pressure and residual water is removed by co-distillation with ethanol under reduced pressure. The residue is triturated with 400 ml. of boiling water. The supernatant is filtered and the CHCl₃ insoluble residue is washed several times with fresh CHCl₃. The washings are filtered. The CHCl₃ solutions are combined, and the CHCl₃ is evaporated under reduced pressure leaving 4.66 g. of glass. The latter is chromatographed on a column of 250 g. of silica gel packed and eluted with a solvent system composed of dichloromethane-methanol [9:1 (v/v)] to yield 3.64 g. of 1,2',6'-tri-N-acetyl-2-epi-fortimicin B 4,5-carbamate (17)]:

[α]_D^{23.2}+31° (c 1%, CH₃OH); i.r. (CDCl₃) 3439, 3320, 1752, 1652 cm⁻¹; NMR (CDCl₃) 1.21 d (J=6.7 Hz, C₆'-CH₃); 1.98, 2.00, 2.03 (COCH₃'s); 2.89 (NCH₃); 3.48 (OCH₃). MS M⁺ Calcd for C₂₂H₃₆N₄O₉: 500.2502; Meas. 500.2502.

EXAMPLE 15

1,2',6'-Tri-N-acetyl-2-O-benzyl-2-epi fortimicin B 4,5-carbamate (18)

To a magnetically stirred suspension of 2.67 g. of 1,2',6'-Tri-N-acetyl-2-epi-fortimicin B 4,5-carbamate (17), 2.22 g. of BaO and 2.86 of Ba(OH) 8H₂O in 134 ml. of N,N-dimethylforamide, cooled in an isopropanol ice bath, is added 2.3 ml. of benzylbromide. The reaction mixture is stirred in the isopropanol ice bath for 15 minutes, and then stirred in an ice bath for 3.5 hours, and then stirred at ambient room temperature overnight. The mixture is filtered through a celite mat. The mat is washed thoroughly with CHCl₃. The filtrates are combined and the solvent is evaporated under reduced pressure. The residue is taken up in CHCl₃ and the CHCl₃ again filtered through a celite mat. The solvent is evaporated under reduced pressure and residual N,N-dimethylformamide is removed by co-distillation with toluene under reduced pressure leaving 3.00 g. of an oil. The latter product is chromatographed on a column of 250 g. of silica gel packed and eluted with a solvent system composed of 1,2-dichloroethane-methanol [9:1 (v/v)] to yield 1.83 g. of 1,2',6'-tri-N-acetyl-2-O-benzyl-2-epi-fortimicin B 4,5-carbamate (18):

[α]_D^{23.2}+52.5° (c 1%, CH₃OH); i.r. (CDCl₃) 3439, 3312, 1742, 1644 cm⁻¹ NMR (CDCl₃) 1.20 (J=6.6 Hz, C₆'-CH₃); 1.90, 1.94; 1.96 (OCOCH₃'s); 2.82 (NCH₃); 3.42 (OCH₃); 4.62, 4.64, (q, OCH₂Ph); 5.14 d (J=3 Hz, C₁'-H); MS M⁺ X1 Calcd for C₂₉H₄₃N₄O₉: 591.3030; Meas. 591.3053; Cyclitol Calcd for C₁₈H₂₅N₂O₆: 365.1713; Meas. 365.1706

EXAMPLE 16

2-O-Benzyl-2-epi-fortimicin B (19)

A solution of 6.39 g. of 1,2',6'-tri-N-acetyl-2-O-benzyl-2-epi-fortimicin B 4,5-carbamate (18) in 800 ml. of 2 N aqueous NaOH is heated at 85 degrees for three days. The resulting solution is cooled to room temperature and brought to pH 7 by addition of 1 N hydrochloric acid. The water is evaporated under reduced pressure. Residual water is removed by co-distillation with ethanol under reduced pressure. The residue is treated with several portions of boiling ethanol, and the supernatants are filtered and combined. The ethanol is evaporated and the residue is treated with several portions of boiling CHCl₃, and the supernatants are filtered and combined. Evaporation of the CHCl₃ leaves 5.53 g. of a glass. The latter product is chromatographed on a column of 450 g. silica gel packed and eluted with a solvent system composed of dichloromethane-methanol-ammonium hydroxide (concentrated) [10:1:1 (v/v/v)] to yield 3.24 g. of 2-O-benzyl-2-epi-fortimicin B (19):

[α]D (c 1%, CH₃OH), i.r. (CDCl₃) 3372, 3292; NMR (CDCl₃) 1.05 d (J=6.3 Hz, C₆'-CH₃), 2.30 (NH₂,s), 2.44 (NCH₃), 3.51 (OCH₃), 4.69 (OCH₂Ph), 4.90 d (J=3.4 Hz, C₁'-H). MS M⁺ Calcd. for C₂₂H₃₈N₄O₅: 438.2842; Meas. 438.2853; Diaminosugar Calcd for C₁₁H₁₉N₂O₃: 227.1396; Meas. 227.1401.

EXAMPLE 17

1,2',6'-Tri-N-benzyloxycarbonyl-2-O-benzyl-2-epi-fortimicin B (20)

To a magnetically stirred solution of 2.51 g. of 2-O-benzyl-2-epi-fortimicin B (19), 28 ml. of water, and 10 ml. of CH OH, cooled in an ice bath, is added 4.4 g. of N-benzyloxycarbonyloxysuccinimide. Stirring is continued with cooling for 3 hours and then at ambient temperature overnight. The resulting solution was poured into 5% aqueous NaHCO₃ and the resulting suspension is extracted with several portions of CHCl₃. The CHCl₃ solutions are combined and dried (MgSO₄). Evaporation of the CHCl₃ leaves 4.64 g. of glass. A sample of 0.998 g. of this material is chromatographed on a column of 100 g. of silica gel packed and eluted with a solvent system composed of ethyl acetate-triethylamine [19.8:0.2 (v/v)] to yield 0.584 g. of 1,2',6'-tri-N-benzyloxycarbonyl-2-O-benzyl-2-epi-fortimicin B (20):

[α]_D^{23.2}+37.2° (c 1%, CH₃OH); i.r. (CDCl₃) 3444, 3347, 1704 cm⁻¹; NMR (CDCl₃) 1.06 d (J=5.9 Hz, C₆'-CH₃); 2.31 (NCH₃); 3.44 (OCH₃).

Analysis Calcd. for C₄₆H₅₆N₄O₁₁: C, 65.69; H, 6.71; N, 6.66; Found: C, 65.13; H, 7.01; N. 6.45.

EXAMPLE 18

Tetra-N-benzyloxycarbonyl-2-O-benzyl-2-epi fortimicin A (21)

To a magnetically stirred solution of 0.500 g. of 1,2',6'-tri-N-benzyloxycarbonyl-2-O-benzyl-2-epi-fortimicin B (20) in 30 ml. of tetrahydrofuran, cooled in an ice bath, is added 0.182 g. of N-(N-benzyloxycarbonyl-glycyloxy)succinimide. Stirring is continued with cooling for 3 hours and then at ambient temperature overnight. The resulting solution is poured into a solution of 5% aqueous $NaHCO_3$, and the suspension is extracted with several portions of $CHCl_3$. The $CHCl_3$ solutions are combined and dried ($MgSO_4$). Evaporation of the $CHCl_3$ leaves 0.607 g. of glass. The latter product (0.600 g.) is chromatographed on a column of 60 g. of silica gel packed and eluted with a solvent system composed of 1,2-dichloroethane-ethyl acetate [1:1 (v/v)] to yield 0.413 g. of tetra-N-benzyloxycarbonyl-2-O-benzyl-2-epi-fortimicin A (21):

$[\alpha]_D$ (c 1%, $CH_3OH$); i.r. ($CDCl_3$) 3433; 3335; 1710, 1640 $cm^{-1}$; NMR ($CDCl_3$) 1.18 d (J=6.8 Hz, $C_6$'-$CH_3$), 2.36 ($NCH_3$), 3.50 ($OCH_3$).

Analysis Calcd. for $C_{56}H_{65}N_5O_{14} \cdot H_2O$: C, 64.04; H, 6.43; N, 6.67 Found: C, 64.46; H, 6.49; N, 6.74.

EXAMPLE 19

2-epi-Fortimicin A Tetrahydrochloride (22)

A. A sample of 1.25 g. of 1,2',6'-tri-N-benzyloxycarbonyl-2-O-benzyl-2-epi-fortimicin A (21) is hydrogenated for 4 hours in 100 ml. of 0.2 N hydrochloric acid in $CH_3OH$ under 3 atmospheres of hydrdogen in the presence of 2.5 g. of 5% Pd/C. The catalyst is removed by filtration and the solvent is evaporated under reduced pressure. Residual hydrochloric acid is removed by co-distillation with $CH_3OH$ under reduced pressure leaving 0.668 g. of 2-epi-fortimicin A tetrahydrochloride (22):

$[\alpha]_D^{22}$ +55° (c 1%, $CH_3OH$); i.r. (KBr) 1640$^{-1}$; NMR ($D_2O$) 1.81 d (J=6.7 Hz, $C_6$'-$CH_3$), 3.63 ($NCH_3$), 4.06 ($OCH_3$), 5.79 d (J=3.7 Hz, $C_6$'-$CH_3$), 3.63 ($NCH_3$), 4.06 ($OCH_3$), 5.79 d (J=3.7 Hz, $C_1$'-H).

MS M+ Calcd for $C_{17}H_{35}N_5O_6$: 405.2587. Meas. 405.2580.

B. A sample of 0.110 g. of tetra-N-benzyloxycarbonyl-2-epi-fortimicin A (11) is hydrogenated for 4 hours in a solution with 19 ml. of 0.1 N hydrochloric acid in methanol under 3 atmospheres of hydrogen in the presence of 0.110 g. of 5% Pd/C. The catalyst is removed by filtration and the solvent is evaporated under reduced pressure. Residual hydrochloric acid is removed by co-distillation with $CH_3OH$ under reduced pressure leaving 63 mg. of 2-epi-fortimicin A tetrahydrochloride (22) identical with that prepared as described above.

EXAMPLE 20

2-O-Glycyl-2-epi-fortimicin A pentahydrochloride (23)

A sample of 0.1819 g. of tetra-N-benzyloxycarbonyl-2-O-[N-benzyloxycarbonylglycyl]-2-epi-fortimicin A (10) is hydrogenated for four hours in a solution with 16 ml. of 0.2 N-hydrochloric acid in $CH_3OH$ and 14 ml. of $CH_3OH$ under 3 atmospheres of hydrogen in the presence of 0.2 g. of 5% Pd/C. The catalyst is removed by filtration and the solvent is evaporated under reduced pressure. Residual hydrochloric acid is removed by co-distillation with $CH_3OH$ under reduced pressure leaving 0.0769 g. of 2-O-glycyl-2-epi-fortimicin A pentahydrochloride (23) as a glass:

$[\alpha]_D^{23}$ +50.5° (c 1%, $CH_3OH$) i.r. (KBr) 1750 $cm^{-1}$; NMR ($D_2O$) 1.82 d (J=6.7 Hz, $C_6$'-$CH_3$), 3.67 ($NCH_3$), 4.02 ($OCH_3$), 5.84 d (J=3 Hz, $C_1$'-H), 6.16 q (J1,2=4 Hz, J2,3=9 Hz, $C_2$-H).

MS M+ Calcd for $C_{19}H_{38}N_6O_7$: 462.2802. Meas. 462.2777; Cyclitol Calcd for $C_{12}H_{23}N_4O_5$: 303.1668. Meas. 303.1672.

EXAMPLE 21

1-N-Glycyl-2-epi-fortimicin A pentahydrochloride (24)

An aqueous of 0.431 g. of 2O-glycol-2-epi-fortimicin A pentahydrochloride (23) is applied to a column of 25 ml. of AG2-X(OH) resin (50–100 mesh). The basic eluate is collected, and the resulting aqueous solution kept at ambient temperature for 1 hour. The resulting solution is then brought to pH 1 by addition of 0.2 N hydrochloric acid. The water is evaporated under reduced pressure and residual water is removed by co-distillation with ethanol and then with ethanol under reduced pressure leaving 0.345 g. of 1-N-glycyl-2-epi-fortimicin A tetrahydrochloride (24).

$[\alpha]_D^{24.5}$ = +68.9° (c 1%, $CH_3OH$), NMR ($D_2O$) 1.82 d (J=7.0 Hz $C_6$'-$CH_3$), 3.64 ($NCH_3$), 4.06 ($OCH_3$); 5.72 (J=3.6 Hz $C_1$'-H), IR (KBr) 1642 $cm^{-1}$, MS M+ Calcd. for $C_{19}H_{38}N_6O_7$: 462.2802; Meas. 462.2777; Cyclitol Calcd. for $C_{12}H_{23}N_4O_5$: 303.1668; Meas. 303.1683. The following reaction schemes are illustrative of processes for making compounds of Examples 22–28.

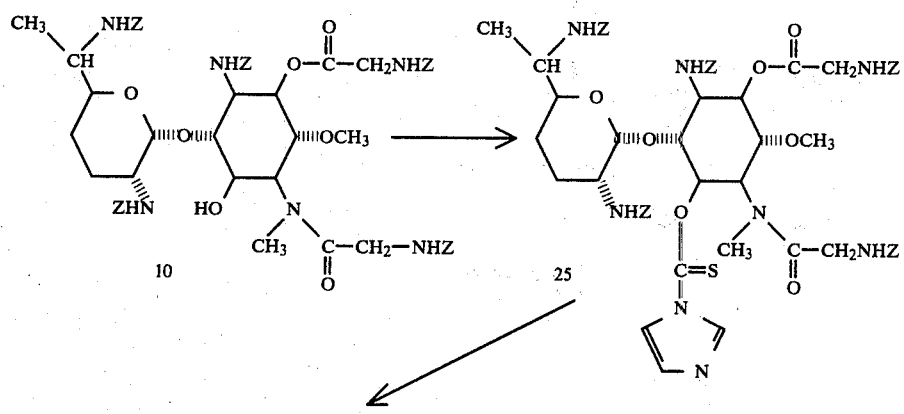

-continued
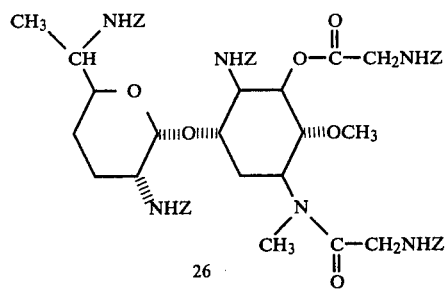
26
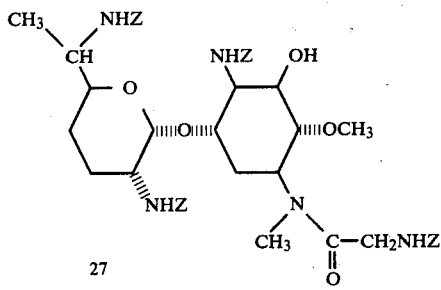
27
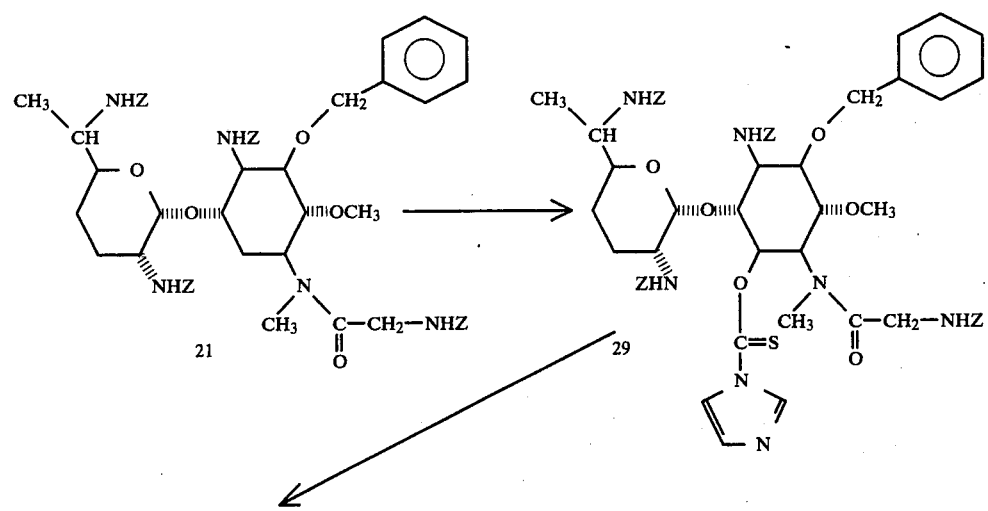
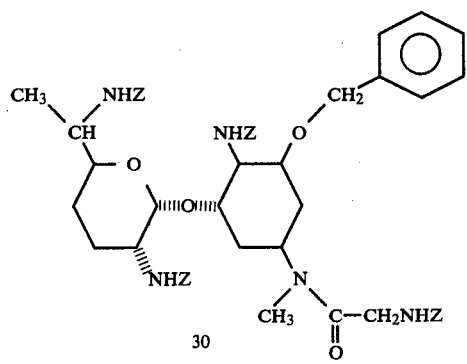
30
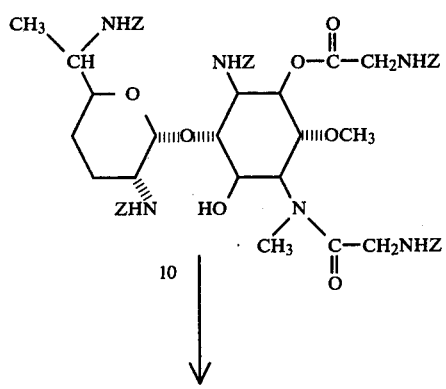
10

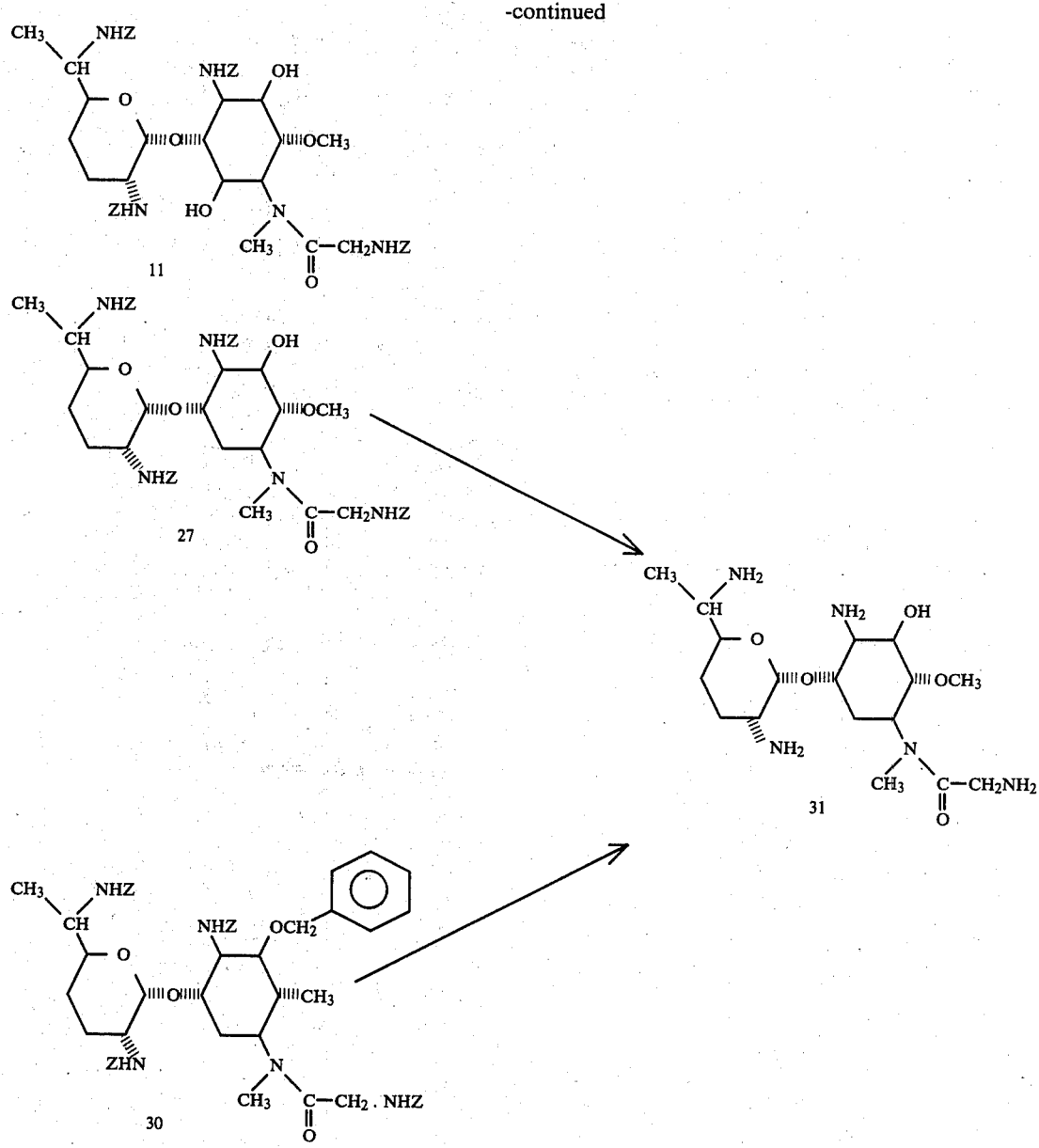

EXAMPLE 22

1,2',6',2'''-tetra-N-benzyloxycarbonyl-2-epi-fortimicin A (11)

A solution of 1.0 g. of 1,2',6',2'''-tetra-N-benzyloxycarbonyl-2-O-(N-benzyloxycarbonylglycyl)-2-epi-fortimicin A (10) 5 ml. of 5% aqueous NaHCO₃, and 50 ml. of CH₃OH is stirred at ambient temperature overnight and then shaken with a mixture of 500 ml. of 5% aqueous NaHCO₃ and 250 ml. of CHCl₃. The CHCl₃ is separated, and the aqueous solution is washed with 250 ml. of CHCl₃. The CHCl₃ solutions are combined and dried (MgSO₄). Evaporation of the CHCl₃ under reduced pressure leaves 0.972 g. of glass. Chromatography of the latter on a column (2.5 cm. O.D.×54 cm.) of 90 g. of silica gel packed and eluted with a solvent system composed of ethyl acetate-hexane [9:1 (v/v)] gave 0.628 g. of 1,2',6',2'''-tetra-N-benzyloxycarbonyl-2-epi-fortimicin A identical with that described above.

EXAMPLE 23

1,2',6',2'''-Tetra-N-benzyloxycarbonyl-2-O-(N-benzyloxycarbonylglycyl)-5-O-thiocarbonylimidazoyl-2-epi-fortimicin A (25)

A solution of 0.600 g. of 1,2',6',2'''-tetra-N-benzyloxycarbonyl-2-O-(N-benzyloxycarbonylglycyl)-2-epi-fortimicin A (10), 0.436 g. of 1,1'-thiocarbonyldiimidazole, 0.6 ml. of triethylamine, and 22 ml. of 1,2-dichloroethane is heated under reflux for 1.5 hr. The solution was cooled and the solvent is evaporated under reduced pressure leaving 1.25 g. of dark brown oil. The latter was chromatographed on a column (2.5×37 cm.) of 60 g. of silica get packed and eluted with ethyl acetate to yield 0.565 g. of pure 1,2',6',2'''-tetra-N-benzyloxycarbonyl-2-O-(N-benzyloxycarbonylglycyl)-5-O-thiocarbonylimidazoyl-2-epi-fortimicin A.

EXAMPLE 24

1,2′,6′,2″-tetra-N-benzyloxycarbonyl-2-O-(N-benzyloxycarbonylglycyl)-5-deoxy-2-epi-fortimicin A (26)

To a magnetically stirred, refluxing solution of 2 ml. of tri-N-butyltin hydride in 45 ml. of dioxane, under an atmosphere of nitrogen, is added, dropwise, a solution of 1,2′,6′,2″-tetra-N-benzyloxycarbonyl-2-O-(N-benzyloxycarbonylglycyl)-5-O-thiocarbonylimidazoyl-2-epi-fortimicin A (10). After the addition was complete, reflux is continued for 2 hours. The resulting solution is cooled to room temperature, and the solvent is evaporated under reduced pressure. Hexane (about 20 ml.) is added and the resulting mixture is kept at room temperature overnight. The hexane supernatant is removed by decantation and the residue is chromatographed on a column (2.5×32 cm.) of 50 g. of silica gel packed and eluted with a solvent system composed of ethyl acetate-hexane (4:1, v/v) to yield 307 mg. of 1,2′,6′,2″-tetra-N-benzyloxycarbonyl-2-O-(N-benzyloxycarbonylglycyl)-5-deoxy-2-epi-fortimicin A.

EXAMPLE 25

1,2′,6′,2″-tetra-N-benzyloxycarbonyl-2-O-benzyl-5-O-thiocarbonylimidazoyl-2-epi-fortimicin A (29)

A magnetically stirred solution of 1,2′,6′,2″-tetra-N-benzyloxycarbonyl-2-O-benzyl-2-epi-fortimicin A (21), 1.31 g. of 1,1′-thiocarbonyldimidazole, 1.3 ml. of triethylamine, and 65 ml. of 1,2-dichloroethane is heated under reflux for 8 hours. The solvent is evaporated under reflux and the residue is chromatographed on a column (3.2×61 cm.) of 200 g. of silica gel packed and eluted with a solvent system composed of ethyl acetate-hexane (9:1 v/v) to yield 1.95 g. of 1,2′,6′,2″-tetra-N-benzyloxycarbonyl-2-O-benzyl-5-O-thiocarbonylimidazoyl-2-epi-fortimicin A (29).

EXAMPLE 26

1,2′,6′,2″-tetra-N-benzyloxycarbonyl-2-O-benzyl-5-deoxy-2-epi-fortimicin A (30)

To a magnetically stirred refluxing solution of 8 ml. of tri-N-butyltin hydride in 150 ml. of dioxane, under an atmosphere of nitrogen, is added dropwise, a solution of 1.95 g. 1,2′,6′,2″-tetra-N-benzyloxycarbonyl-2-O-benzyl-5-O-thiocarbonylimidazoyl-2-epi-fortimicin A (29). After the addition is complete, heating is continued for 2 hours. The resulting solution is cooled to room temperature, and the dioxane is evaporated under reduced pressure. Hexane (60 ml.) is added and the resulting mixture is kept at room temperature overnight. The hexane is removed by decantation, and the residue (2.9 g.) is chromatographed on a column (2.5×76 cm.) of silica gel packed and eluted with ethyl acetate-hexane (7:3, v/v) to yield 0.694 g. of 1,2′,6′,2″-tetra-N-benzyloxycarbonyl-2-O-benzyl-5-deoxy-2-epi-fortimicin A (30).

EXAMPLE 27

1,2′,6′,2″-tetra-N-benzyloxycarbonyl-5-deoxy-2-epi-fortimicin A (27)

A solution of 0.270 g. of 1,2′,6′,2″-tetra-N-benzyloxycarbonyl-2-O-(N-benzyloxycarbonylglycyl)-5-deoxy-2-epi-fortimicin A (27), 1.6 ml. of 5% aqueous NaHCO$_3$, and 160 ml. of CH$_3$OH is stirred at ambient temperature for two days and then shaken with a mixture of 100 ml. of 5% aqueous NaHCO$_3$ and 50 ml. of CHCl$_3$. The CHCl$_3$ solution is separated, and the aqueous solutions are washed with two 50 ml. portions of CHCl$_3$. The CHCl$_3$ solutions are combined and dried (MgSO$_4$). Evaporation of the CHCl$_3$ under reduced pressure leaves 0.253 g. of glass. Chromatography of the latter product (0.218 g.) on a column (1.8×32 cm.) of 25 g. of silica gel packed and eluted with ethyl acetate gave 0.139 g. of 1,2′,6′,2″-tetra-N-benzyloxycarbonyl-5-deoxy-2-epi-fortimicin A (27).

EXAMPLE 28

2-epi-5-Deoxyfortimicin A (31)

A. A sample of 0.579 g. of 1,2′,6′-2″-tetra-N-benzyloxycarbonyl-2-epi-5-deoxyfortimicin A (27) in 50 ml. of 0.2 N hydrochloric acid in methanol was hydrogenated for 3 hours thru atmospheres of hydrogen for 4 hours in the presence of 0.58 g. of 5% palladium on carbon. The catalyst was removed by filtration and solvent was evaporated under reduced pressure leaving 0.307 g. of 2-epi-5-deoxy-fortimicin B (31) as the tetrahydrochloride salt. An aqueous solution of the latter was passed through a column of 16 ml. of AG 1-X2 (SO$_4$) resin (50–100 mesh) contained in a 50 ml. buret. Lyophilization of the product containing eluate gave 0.319 g. of 2-epi-5-deoxyfortimicin A (31) as the disulfate salt: [α]$_D$.

B. A sample of 0.514 mg. of 1,2′,6′,2″-tetra-N-benzyloxycarbonyl-2-O-benzyl-2-epi-fortimicin A (30) in 50 ml. of 0.2 N hydrochloric acid in methanol was hydrogenated for 3 hours under three atmospheres of hydrogen in the presence of 1.0 g. of 5% palladium on carbon. The catalyst was removed by filtration and the solvent was evaporated under reduced pressure leaving 0.262 mg. of 2-epi-5-deoxyfortimicin A (31) as the tetrahydrochloride salt. An aqueous solution of the latter was passed through 17 ml. of AG 1-X2 (SO$_4$) contained in a 25 ml. buret. Lyophilization of the eluate containing the product gave 2-epi-5-deoxy-fortimicin A (31) as the disulfate salt identical with that prepared as described above from 1,2′,6′,2″-tetra-N-benzyloxycarbonyl-2-epi-fortimicin A (31). charcoal (0.3 g., 5%) under three atmospheres of hydrogen for four hours. The mixture is filtered and the filtrate is concentrated under vacuum with several additions and removals of methanol to yield 1-epi-3-O-demethylfortimicin A tetrahydrochloride (165 mg.).

EXAMPLE 29

2-Epi-fortimicin A tetrahydrochloride in vitro Antibiotic Activity

The in vitro antibiotic activity is determined by a 2-fold agar dilution method using 10 ml. per petri place of Mueller-Hinton Agar. The agar is inoculated with one loopful (0.001 ml. loop) of a 1:10 dilution of a 24 hour broth culture of the indicated test organism and incubated at 37° for 24 hours. The activity of 2-epi-fortimicin A tetrahydrochloride is tabulated below and expressed as the (M.I.C.) minimum inhibitory concentration (mcg./ml.)

| Organism | M.I.C. |
| --- | --- |
| Staph. aureus Smith | 1.56 |
| Strep. faecalis 10541 | 50 |
| Enterobacter aerogenes 13048 | 25 |
| E. coli JUHL | 25 |
| E. coli BL 3676 (Res) | 25 |

-continued

| Organism | M.I.C. |
|---|---|
| E. coli 76-2 | 6.2 |
| Kleb. pneumoniae 10031 | 6.2 |
| Kleb. pneumoniae KY 4262 | 6.2 |
| Providencia 1577 | 6.2 |
| Pseudo. aeruginosa BMH #10 | 0.78 |
| Pseudo. aeruginosa KY 8512 | 25 |
| Pseudo. aeruginosa KY 8516 | 50 |
| Pseudo. aeruginosa 209 | >100 |
| Pseudo. aeruginosa 27853 | 25 |
| Sal. typhimurium Ed. #9 | 1.56 |
| Serratia marcescens 4003 | 1.56 |
| Shigella sonnei 9290 | 12.5 |
| Proteus rettgeri U6333 | 25 |
| Proteus vulgaris JJ | 3.1 |
| Proteus mirabilis Fin. #9 | 6.2 |

What is claimed is:

1. A compound selected from the group consisting of 2-epi-fortimicin A, 2-epi-fortimicin B or a 2-epi-fortimicin B derivative represented by the formula:

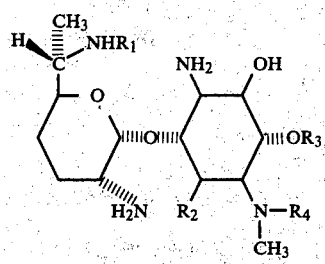

wherein $R_1$ is hydrogen or loweralkyl; $R_2$ is hydrogen or hydroxy; $R_3$ is methyl or hydrogen; and $R_4$ is selected from the group consisting of hydrogen, loweralkyl, aminoloweralkyl diaminolowcralkyl, N-loweralkylaminoalkyl, N,N-diloweralkylaminoloweralkyl, hydroxyloweralkyl, aminohydroxyloweralkyl, N-loweralkylaminohydroxyloweralkyl, N,N-diloweralkylaminohydroxyloweralkyl, acyl of the formula

wherein $R_5$ is loweralkyl, aminoacyl, diaminoloweracyl, diaminoacyl, hydroxyacyl, N-loweralkylaminoacyl, N,N-diloweralkylaminoacyl, hydroxy-substituted amino acyl; and the pharmaceutically acceptable salts thereof.

2. A compound of claim 1 wherein $R_2$ is hydroxy.

3. A compound of claim 2 wherein $R_1$ is loweralkyl.

4. A compound of claim 2: 2-epi-fortimicin A or a pharmaceutically acceptable salt thereof.

5. A compound of claim 4: 2-epi-fortimicin A sulfate.

6. A compound of claim 2: 2-epi-fortimicin B or a pharmaceutically acceptable salt thereof.

7. A compound of claim 1: 2-epi-3-O-demethylfortimicin A or a pharmaceutically acceptable salt thereof.

8. A compound of claim 7: 2-epi-3-O-demethylfortimicin A sulfate.

9. A fortimicin intermediate represented by the formula:

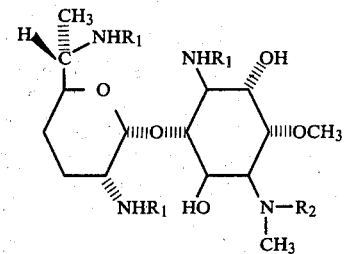

wherein $R_1$ is hydrogen or monocyclicaryloxycarbonyl or acetyl; and $R_2$ is carboethoxy.

10. A compound of claim 9: 1,2',6'-tri-N-acetyl-4-N-ethoxycarbonyl-fortimicin B.

11. A 2-epi-fortimicin intermediate represented by the formula:

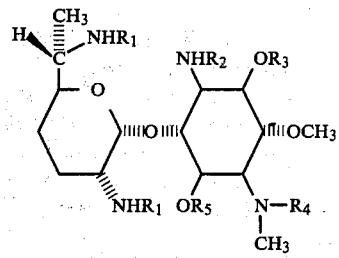

wherein $R_1$ is hydrogen, monocyclicaryloxycarbonyl, acyl of the formula

wherein Y is loweralkyl, or loweralkyl; $R_2$ is hydrogen, monocyclicaryloxycarbonyl or acyl of the formula

$R_3$ is hydrogen, N-benzyloxycarbonylglycyl, glycyl, benzyl or substituted benzyl; $R_4$ is hydrogen, N-benzyloxycarbonylglycyl or glycyl; $R_5$ is hydrogen; $R_2$ and $R_3$ when taken together form a cyclic benzyloxyoxazoline, a cyclic carbamate or a cyclic methyloxazoline moiety; $R_2$ and $R_4$ when taken together form a cyclic urea moiety; and $R_4$ and $R_5$ when taken together form a cyclic carbamate moiety.

12. A compound of claim 11 wherein $R_4$ and $R_5$ are taken together to form a cyclic carbamate moiety.

13. A compound of claim 12: 1,2',6'-tri-N-benzyloxycarbonyl-2-epi-fortimicin B-4,5-carbamate.

14. A compound of claim 11 wherein $R_2$ and $R_3$ are taken together to form a cyclic carbamate and $R_4$ and $R_5$ are taken together to form a cyclic carbamate.

15. A compound of claim 14: 2',6'-di-N-benzyloxycarbonyl-2-epi-fortimicin B-1,2,4,5-biscarbamate.

16. A compound of claim 14: 2-epi-fortimicin B 1,2,4,5-biscarbamate or a pharmaceutically acceptable salt thereof.

17. A compound of claim 11 wherein $R_2$ and $R_3$ taken together form a cyclic benzyloxyoxazolidine moiety and $R_4$ and $R_5$ together form a cyclic carbamate moiety.